(12) United States Patent
West et al.

(10) Patent No.: US 7,679,884 B2
(45) Date of Patent: Mar. 16, 2010

(54) ORGANOSILICON PHOSPHORUS-BASED ELECTROLYTES

(75) Inventors: Robert C. West, Madison, WI (US); Lingzhi Zhang, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 47 days.

(21) Appl. No.: 12/181,458

(22) Filed: Jul. 29, 2008

(65) Prior Publication Data

US 2010/0029970 A1 Feb. 4, 2010

(51) Int. Cl.
*H01G 9/00* (2006.01)
(52) U.S. Cl. ............... 361/502; 429/313; 429/338; 429/33; 556/470; 556/467; 556/13
(58) Field of Classification Search ......... 429/313; 556/470, 467, 13
See application file for complete search history.

(56) References Cited

U.S. PATENT DOCUMENTS 4,607,115 A * 8/1986 Riederer et al. ............. 556/462
2007/0076349 A1 4/2007 Dementiev et al.

OTHER PUBLICATIONS

Rozengart et al., {Interaction of cholinesterase of the commodore squid (*Berryteuthis magister*) individuals from different habitat zones with reversible onium inhibitors, Journal of Evolutionary Biochemistry and Physiology (Translation of Zhurnal Evolyutsionnoi Biokhimii I Fiziologii) (1997), 33(3), 322-331}.*

Hatanaka et al., {Single-step synthesis of cyclopentenones from (3-alkoxycarbonyl-2-oxo propylidene)triphenylphosphorane and 1,2-diacylethylenes, Tetrahedron Letters (1996), 37(3), 401-404}.*
Brovko et al., {Silicon-containing ammonium and phosphonium salts, Zhurnal Obshchei Khimii (1983), 53(8), 1831-4}.*
Marshall et al., {Total Synthesis of (–)-Callystatin A, Journal of Organic Chemistry (2002), 67(9), 2751-2754}.*
Hatanaka et al., {Single-step synthesis of cyclopentenones from (3-alkoxycarbonyl-2-oxo propylidene)triphenylphosphorane and 1,2-diacylethylenes, Tetrahedron Letters (1996), 37(3), 401-4}.*
Rozengardt et al., {Organoelement onium reversible cholinesterase inhibitors, Khim. Primen. Elementoorg. Soedin. (1990), 92-7}.*
Skvortsov et al., {Hydrosilylation in the presence of fixed nickel complexes, Zhurnal Obshchei Khimii (1988), 58(8), 1831-40}.*
E. Frackowiak et al., Room-temperature Phosphonium Ionic Liquids for Supercapacitor Application, 164104-1-164104-3 (86 Applied Physics Letters)(2005).
A. Balducci, The Use Of Ionic Liquids As Solvent-free Green Electrolytes for Hybrid Supercapacitors, 82 Applied Physics 627-632 (2006).
S. Ambasht et al., Preparation of Trimethylsilylmethyl Derivatives Using Phase Transfer Methods, 318-320 J. Synthesis (1980).
U. Yoon, et al., Applications of Phthalimide Photochemistry to Macrocyclic Polyether, Polythioether and Polyamide Synthesis, 66 J. Org. Chem. 939-943 (2001).

* cited by examiner

*Primary Examiner*—Porfirio Nazario Gonzalez
*Assistant Examiner*—Chukwuma O Nwaonicha
(74) *Attorney, Agent, or Firm*—Quarles & Brady LLP

(57) ABSTRACT

Disclosed are electrolytes that are organosilicon phosphorus-based, and supercapacitors which incorporate them. These electrolytes are cationic salts with a phosphorous containing organosilicon moiety. They appear particularly suitable for use in applications such as electric and hybrid electric vehicles.

10 Claims, 3 Drawing Sheets

FIG. 4

| Compound | η (cP) | $T_g$ (°C) | $T_{s\text{-}s}/T_c$ (°C) | $T_m$ (°C) | σ (mS/cm) | Flammable |
|---|---|---|---|---|---|---|
| TMSC1PILTFSI | - | na | 27[a] | 43 | | no |
| TMSC1PILBOB | - | na | 31[a] | 41 | | no |
| TMSCOCPILTFSI | 70 | -80 | na | na | 1.672 | no |
| TMSCOCPILBOB | - | -45 | na | na | 0.677 | no |
| TMSC3PILTFSI | 100 | -64 | na | na | 0.638 | no |
| TMSC3PILBOB | 224 | -44 | na | na | | no |
| TMSCOC2PILTFSI | 98 | -76 | na | -na | | no |
| TMSCOC2PILPF6 | - | na | na | 100 | | no |
| TMSCOC2PILNCN | - | na | -21[b] | 37 | | no |

- a: solid-solid phase transition; b: crystallization process.

ORGANOSILICON PHOSPHORUS-BASED ELECTROLYTES

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to ionic liquids useful as electrolytes in connection with energy storage devices such as supercapacitors. More particularly, it relates to organosilicon phosphorus electrolytes.

Supercapacitors, sometimes also referred to in the literature as "electric double-layer capacitors", "electrochemical capacitors" or "ultracapacitors" are well known. Supercapacitors provide energy storage as well as pulse power delivery. This is useful in many applications, such as in connection with automotive starters and hybrid automotive vehicles.

One well known type of supercapacitor is depicted in FIG. 1. This drawing shows a supercapacitor 10 having two electrodes 11 which are kept from electrical contact with each other by a separator 12. There are current collectors 13 at opposite ends of the device. The electrodes consist of a porous material 14 and an electrolyte 15. Both the separator 12 and the porous material 14 are typically immersed in the electrolyte 15.

Current collecting plates 13 are in contact with the electrodes 11. Electrostatic energy is stored in polarized liquid layers, which form when a potential is applied across two of the electrodes. A "double layer" of positive and negative charges is formed at the electrode-electrolyte interface. The electrolyte allows ions to move freely through the separator.

To be optimally effective for certain applications, supercapacitors must, among other properties, have low internal resistance, store large amounts of charge, be physically strong, be stable at desired (preferably high) voltages, and be otherwise compatible with the usage environment. Therefore, there are many design parameters that must be considered in construction of such devices.

Aqueous and some organic electrolyte solutions have been proposed for use in supercapacitors. Aqueous electrolytes provide relatively low series resistance, improving the time constant of a supercapacitor and providing high power densities. However, they are often not stable at the operating voltages exceeding the electrolysis voltage of water (1.23 V).

Organic liquid electrolytes used in supercapacitors should preferably have higher ionic conductivity. As an example, acetonitrile provided high ionic conductivity. However, acetonitrile is a hazardous flammable and toxic material, which produces highly toxic products (HCN and CO) upon combustion and thermal decomposition.

Some other previously used organic liquid electrolytes have been based on alkyl carbonates (ethylene carbonate, propylene carbonate, and γ-butyro-lactone, or dimethylcarbonate, diethylcarbonate, and ethylmethylcarbonate, for example) which are highly flammable. Some also have lower ionic conductivity as compared to aqueous electrolytes or electrolytes based on acetonitrile, and this causes higher internal losses of stored energy and power density of the supercapacitor.

In A. Balducci, The Use of Ionic Liquids As Solvent-free Green Electrolytes For Hybrid Supercapacitors, 82 Applied Physics 627-632 (2006), there was a discussion of using $(CF_3SO_2)_2N^-$ ("TFSI") as an anion portion of salts containing cyclic cationic nitrogen moieties, as electrolytes for supercapacitors.

Our laboratory also recently reported, in U.S. patent application publication 2007/0076349, that polysiloxanes could have utility as electrolytes for supercapacitors and other energy storage devices.

In Z. Li et al., A New Room Temperature Ionic Liquid 1-butyl-3-trimethylsilylimidazolium Hexafluorophosphate As A Solvent For Extraction And Preconcentration Of Mercury With Determination By Cold Vapor Atomic Absorption Spectrometry, 71 Talanta 68-72 (2007) there was a discussion of using $PF_6^-$ as an anion with a cationic organosilicon compound having a cyclic nitrogen containing moiety, as a solvent for extraction.

In U.S. Ser. No. 11/865,089, filed Oct. 1, 2007, we recently reported on the use of organosilicon amine-based electrolytes, primarily for use in energy storage devices such as supercapacitors. These have certain advantages. However, still other improvements are desired with respect to electrolytes having varied properties.

In E. Frackowiak et al., Room-temperature Phosphonium Ionic Liquids For Supercapacitor Application, 164104-1-164104-3 (86 Applied Physics Letters) (2005) there was a discussion of using phosphonium salts for supercapacitor electrolytes, where the anion for such salts was $(CF_3SO_2)_2N^-$.

Notwithstanding these developments in the art, there is a need for additional improvements with respect to electrolytes for supercapacitors and batteries, particularly with respect to providing electrolytes which do not have high flammability and have high thermal stability.

SUMMARY OF THE INVENTION

In one aspect the invention provides an electrolyte comprising the following cationic moiety:

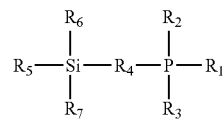

$R_1$, $R_2$ and $R_3$ are the same or different, and each is selected from the group consisting of alkyl moieties of less than ten carbons and hydrogen. $R_4$ is selected from the group consisting of alkyl moieties of less than ten carbons (e.g. $CH_2$ or $C_3H_6$) and alkoxy groups of less than ten carbons.

$R_5$, $R_6$ and $R_7$ are the same or different and each is selected from the group consisting of alkyl moieties of less than ten carbons, hydrogen and —O—$SiR_8R_9R_{10}$. $R_8$, $R_9$ and $R_{10}$ are the same or different and each is selected from the group consisting of alkyl moieties with less than ten carbons and hydrogen.

In such compounds there are four carbons directly linked to the phosphorus and they are only linked to each other through the phosphorus. This is highly desirable in connection with these compounds.

In a preferred form all of $R_1$, $R_2$ and $R_3$ are alkyl moieties with less than three carbons, $R_4$ is selected from the group consisting of alkyl moieties with less than three carbons, and $R_8$, $R_9$ and $R_{10}$ are all selected from the group consisting of alkyl moieties with less than three carbons. Even more preferably all of the R groups are alkyl moieties, all of them but $R_4$ are —$CH_3$ or —$C_2H_5$, and $R_4$ is $(CH_2)_n$ with n being less than 5.

These cations will be presented in supercapacitors (or possibly batteries) as a portion of the electrolyte (together with an anion to create a salt). Especially preferred anions are halogen anions, $(CF_3SO_2)_2N^-$, $B(C_2O_4)_2^-$ and tetrafluoroborate anion, with $(CF_3SO_2)_2N^-$ being most preferred.

In another aspect the invention provides an electrochemical double-layer capacitor where the electrolyte is present as part of the supercapacitor's electrode system. This is expected to enable such a supercapacitor to operate at high voltages for extended periods.

The electrolytes of the present invention should have high room temperature ionic conductivity (hence providing low series resistance), high thermal and electrochemical stability, and low volatility, toxicity and flammability.

In another aspect the invention provides a quaternary phosphonium salt having the following formula:

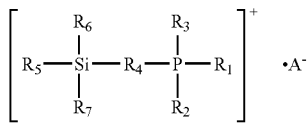

$R_1$, $R_2$ and $R_3$ are the same or different, and each is selected from the group consisting of alkyl moieties of less than ten carbons. $R_4$ is selected from the group consisting of alkyl moieties of less than ten carbons (e.g. $CH_2$ or $C_3H_6$) and alkoxy groups of less than ten carbons.

$R_5$, $R_6$ and $R_7$ are the same or different and each is selected from the group consisting of alkyl moieties of less than ten carbons, hydrogen and —O—$SiR_8R_9R_{10}$. $R_8$, $R_9$ and $R_{10}$ are the same or different and each is selected from the group consisting of alkyl moieties with less than ten carbons and hydrogen. Also, A is an anion.

Our preferred electrolytes are relatively easy to make, and can be synthesized in high yields from available and relatively inexpensive starting materials. They are also stable in storage and processing.

The above and still other advantages of the present invention will be apparent from the description that follows. It should be appreciated that the following description is merely of the preferred embodiments of our invention. The claims should therefore be looked to in order to understand the full claimed scope of the invention.

BRIEF DESCRIPTION OF THE DRAWINGS

FIG. 4 summarizes test results on compounds of the present invention.

DESCRIPTION OF THE PREFERRED EMBODIMENTS

The electrolytes of the present invention have utility in a variety of energy storage devices. We prefer using them primarily in supercapacitors, albeit there may be utility in other devices such as batteries and fuel cells.

We propose substituting our electrolytes for known liquid electrolytes in prior art conventional, or other, supercapacitors. The exact structure of the supercapacitors, apart from the electrolyte we propose to use therewith, does not appear critical.

Figure 1:
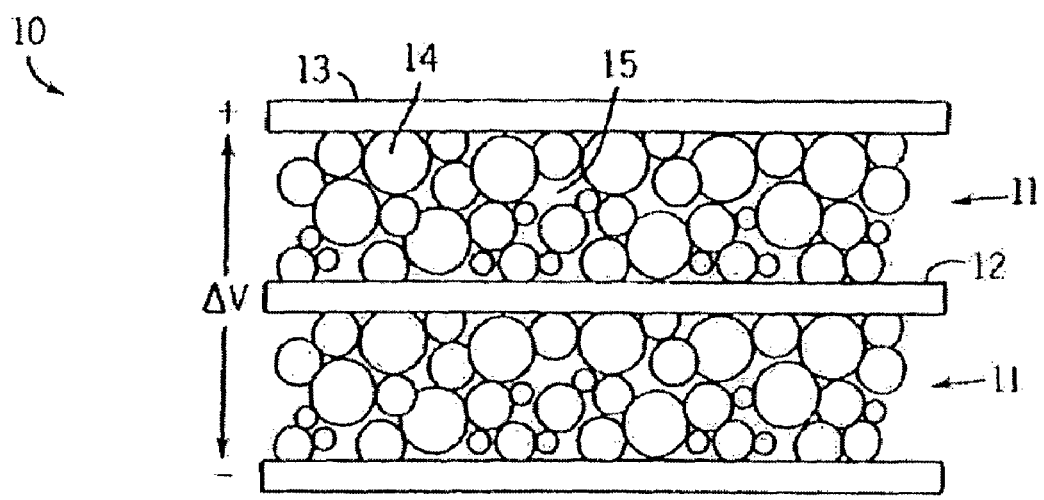
FIG. 1 depicts, in schematic form, a known structure for a supercapacitor.

For example, one could use a FIG. 1 type supercapacitor. Details about this type of supercapacitor can be obtained from U.S. patent application publication 2007/0076349, the disclosure of which is incorporated by reference herein as if fully set forth herein.

Such supercapacitors may have electrodes made in part of porous or other structured materials so that an electrolyte can easily penetrate the pores/structures, facilitating rapid ion motion and high conductivity. Electrons can then easily flow from the electrode to the current collector and vice versa. Nanostructured carbon electrodes are preferred.

Separators between electrodes for use in the supercapacitors of the present invention can be of conventional structure. For example, they can be made of polymer film of porous structure such as PE, PP, or PTFE films, or other known materials which have been used as a separator in a supercapacitor.

On the exterior surface of the electrode/separator "sandwich" we prefer to position current collectors which are electro-conductive metal plates or films, like aluminum, nickel, copper, molybdenum, titanium, steel, or any other known electro-conductive material which can be used as a current collector in supercapacitors.

Synthesis of Intermediates

Figure 2:
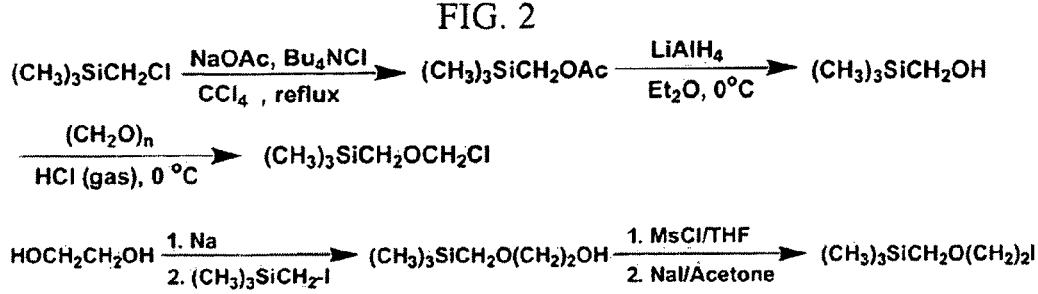
FIG. 2 depicts syntheses, in schematic form, of intermediates useful for the purposes of developing compounds of the present invention.

FIG. 2 depicts schematically the synthesis of two intermediates. We first acquired trimethylsilylmethyl chloride from Gelest Inc. and then obtained trimethylsilylmethyl iodide by refluxing trimethylsilylmethyl chloride with NaI solution in acetone.

We converted the trimethylsilylmethyl chloride to acetatemethyltrimethylsilane generally following the procedure of S Ambasht et al. 318 J. Synthesis (1980). To a suspension of NaOAc (18.5 g, 0.22 mol) and tetrabutylammoniumchloride (2.8 g, 1.0 mmol) in 300 mL carbontetrachloride was added chloromethylpentamethyl disiloxane. (40.0 g, 0.20 mol). The mixture was heated to reflux for 3 days. The solid salt was removed by filtration. After removing the solvent, the pure product was obtained by distillation. Yield: 24 g (80%); b.p. 123-125° C.

Then, to a suspensions of $LiAlH_4$ (7.0 g, 0.184 mol) in 500 mL dry ethyl ether was added the acetatemethyltrimethylsilane (26.3 g, 0.174 mol) dropwise at 0° C. After addition, the mixture was stirred at room temperature for 24 hours. The resulting reaction mixture was then poured cautiously onto ice. The organic phase was separated, and washed with 5% $H_2SO_4$ solution and then water to neutral. The ether solution was dried over magnesium sulfate, filtered, and distilled to give hydroxymethyltrimethylsilane intermediate. Yield: 16 g (88%).; b.p. 118-120° C.

Trimethylsilylmethoxymethyl chloride was synthesized from the hydroxymethyltrimethylsilane intermediate as schematically depicted in FIG. 2. In this regard, a mixture of hydroxymethyltrimethylsilane (40 g, 0.39 mol) and paraformaldehyde (14 g, 0.47 mol) was bubbled with HCl gas at 0° C. for 4 hours. The product was diluted with 200 ml pentane, and then dried over $MgSO_4$. After evaporating the solvent, the product was obtained by distillation in colorless liquid Yield: 50 g (84%); b.p. 135-136° C.

Alternatively, we created a hydroxytrimethylsilylmethyoxyethyl intermediate from the trimethylsilylmethyl iodide as shown. Trimethylsilylmethoxymethyl iodide was synthesized by generally following procedures analogous to those of U Yoon, et al. 66 J. Org. Chem. 939-943 (2001). Trimethylsilylmethoxymethyl iodide was obtained as a colorless liquid. b.p. 118-120° C.

Synthesis of Electrolytes

Once we obtained the organosilicon halides of interest, we reacted selected phosphines (e.g. triethylphosphine, with suitable silanehalides (e.g. trimethylsilylmethoxyethyl iodide) in a suitable solvent (e.g. THF). The resulting silicon-containing phosphonium based halides were precipitated from dry ether, and purified by recrystallization from $CHCl_3$/$Et_2O$. For example, we created using these techniques the following four halide compounds:

EXAMPLE 1

TMSC1PILI

The specific synthesis of the Example 1 compound was: To a 1.0M solution of triethylphosphine (50 mL, 0.1 mol) in THF was added trimethylsilylmethyl iodide (23, 0.11 mol). Then, the reaction was heated to reflux for 8 hours. The product was precipitated from dry ether, and purified by recrystallization from $CHCl_3$/$Et_2O$ to yield ($[CH_3]_3SiCH_2P[CH_2CH_3]^+_3I^-$).

EXAMPLE 2

TMSCOCPILCl

The specific synthesis of the Example 2 compound was: To a 1.0M solution of triethylphosphine (100 mL, 0.2 mol) in THF was added trimethylsilylmethoxymethyl chloride (16 g, 0.11 mol). Then the reaction was heated to reflux for 18 h. The product was precipitated from dry ether, and purified by recrystallization from $CHCl_3$/$Et_2O$ to yield ($[CH_3]_3SiCH_2OCH_2P[CH_2CH_3]^+_3Cl^-$)

EXAMPLE 3

TMSC3PILI ($[CH_3]_3Si[CH_2]_3P[CH_2CH_3]^+_3I^-$)

EXAMPLE 4

TMSCOC$_2$PILI  ($[CH_3]_3SiCH_2OCH_2P[CH_2CH_3]^+_3I^-$)

Figure 3:
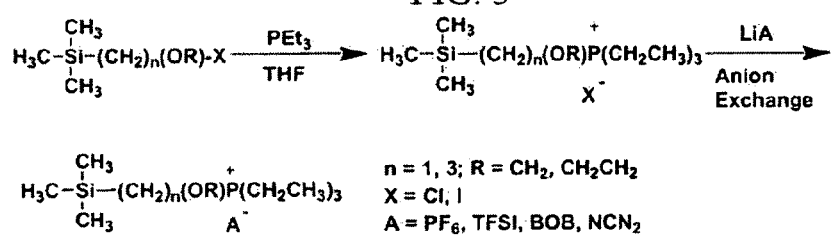
FIG. 3 depicts a synthesis, in schematic form, of how one can use these intermediates to synthesize cations and compounds of the present invention.

If desired, the anion can then be swapped out of the halide compounds using the techniques depicted in FIG. 3. For example, silicon-containing phosphonium halide salts (20 g) and a suitable lithium salt (1.1 equ.) with a specified anion (e.g. $PF_6$, TFSI, BOB (bis(oxalato) borate anion), $NCN_2$, $BF_4$) were dissolved in 50 ml dried acetone to cause an anion exchange. The reaction mixture was stirred at room temperature for 4 hours.

After removing the solvent by rotary evaporation, the residue was dissolved in chloroform/water mixture. The organic phase was separated, washed subsequently with water, dilute sodium thiosulfate solution, dilute $AgNO_3$ solution and water, and then dried over $MgSO_4$. The product was thoroughly dried in vacuo at 100° C. for 48 hours.

This resulted in the following alternative embodiments:

EXAMPLE 5

TMSC1PILTFSI

This is the Example 1 compound with TFSI replacing the I anion.

EXAMPLE 6

TMSC1PILBOB

This is the Example 1 compound with BOB replacing the I anion.

EXAMPLE 7

TMSCOCPILTFSI

This is the Example 2 compound with TFSI replacing the Cl anion.

EXAMPLE 8

TMSCOCPILBOB

This is the Example 2 compound with BOB replacing the Cl anion.

EXAMPLE 9

TMSC3PILTFSI

This is the Example 3 compound with TFSI replacing the I anion.

EXAMPLE 10

TMSC3PILBOB

This is the Example 3 compound with BOB replacing the I anion.

EXAMPLE 11

TMSCOC2PILTFSI

This is the Example 4 compound with TFSI replacing the I anion.

EXAMPLE 12

TMSCOC2PILPF6

This is the Example 4 compound with $PF_6$ replacing the I anion.

EXAMPLE 13

TMSCOC2PILNCN2

This is the Example 4 compound with $NCN_2^-$ replacing the I anion.

Test Results

In the FIG. 4 table are listed various test results on the above compounds, measuring viscosity, transition temperatures, conductivity, and flammability. Note that these tests confirm that these compounds are generally inflammable, appear to have good conductivity, and appear to have desirable transition temperatures and viscosity properties.

While various embodiments of the present invention have been described above, the present invention is not limited to just these disclosed examples. There are other modifications that are meant to be within the scope of the invention and claims. For example, it is expected that a variety of other organosilicon phosphorus-based compounds will also have desirable electrolyte characteristics.

Thus, the claims should be looked to in order to judge the full scope of the invention.

INDUSTRIAL APPLICABILITY

The present invention provides improved electrolytes, primarily for use in supercapacitors.

We claim:

1. An electrolyte comprising a cationic moiety comprising the following structure:

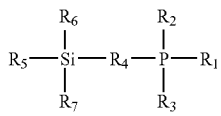

wherein $R_1$, $R_2$ and $R_3$ are the same or different and each is selected from the group consisting of alkyl moieties of less than ten carbons and hydrogen, wherein at least one of $R_1$, $R_2$ and $R_3$ are alkyl moieties;

wherein $R_4$ is selected from the group consisting of alkyl moieties of less than ten carbons, and alkoxy groups of less than ten carbons;

wherein $R_5$, $R_6$ and $R_7$ are the same or different and each is selected from the group consisting of alkyl moieties of less than ten carbons, hydrogen and —O—$SiR_8R_9R_{10}$, wherein $R_8$, $R_9$ and $R_{10}$ are the same or different and each is selected from the group consisting of alkyl moieties with less than ten carbons and hydrogen;

wherein the electrolyte further comprises an anion such that the cationic moiety is present in a salt; and wherein the anion is selected from the group consisting of halogen anions, $(CF_3SO_2)_2N^-$, $B(C_2O_4)_2^-$ and tetrafluoroborate anion.

2. The electrolyte of claim 1, wherein the anion is $(CF_3SO_2)_2N^-$.

3. The electrolyte of claim 2, wherein all of $R_1$, $R_2$ and $R_3$ are alkyl moieties with less than three carbons.

4. The electrolyte of claim 2, wherein $R_4$ is selected from the group consisting of alkyl moieties with less than three carbons.

5. The electrolyte of claim 2, wherein $R_8$, $R_9$ and $R_{10}$ are selected from the group consisting of alkyl moieties with less than three carbons.

6. The electrolyte of claim 2, wherein all of $R_1$, $R_2$, $R_3$, $R_4$, $R_5$, $R_6$, $R_7$ $R_8$, $R_9$ and $R_{10}$ are alkyl moieties.

7. The electrolyte of claim 6, wherein all of $R_1$, $R_2$, $R_3$, $R_5$, $R_6$, $R_7$ $R_8$, $R_9$ and $R_{10}$ are —$CH_3$ or —$C_2H_5$.

8. The electrolyte of claim 2, wherein $R_4$ is $(CH_2)_n$ and n is less than 5.

9. An electrochemical double-layer capacitor comprising an electrolyte comprising:

a cationic moiety comprising the following structure:

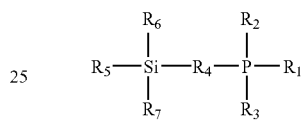

wherein $R_1$, $R_2$ and $R_3$ are the same or different and each is selected from the group consisting of alkyl moieties of less than ten carbons and hydrogen, wherein at least one of $R_1$, $R_2$ and $R_3$ are alkyl moieties;

wherein $R_4$ is selected from the group consisting of alkyl moieties of less than ten carbons, and alkoxy groups of less than ten carbons; and wherein $R_5$, $R_6$ and $R_7$ are the same or different and each is selected from the group consisting of alkyl moieties of less than ten carbons, hydrogen and —O—$SiR_8R_9R_{10}$, wherein $R_8$, $R_9$ and $R_{10}$ are the same or different and each is selected from the group consisting of alkyl moieties with less than ten carbons and hydrogen.

10. The electrochemical double-layer capacitor of claim 9, wherein the capacitor is capable of operating at a voltage of 5.0 volts or above.

* * * * *

UNITED STATES PATENT AND TRADEMARK OFFICE
CERTIFICATE OF CORRECTION

PATENT NO. : 7,679,884 B2
APPLICATION NO. : 12/181458
DATED : March 16, 2010
INVENTOR(S) : Robert C. West et al.

It is certified that error appears in the above-identified patent and that said Letters Patent is hereby corrected as shown below:

In claim 1, at line 45 of column 7, delete "halogen anions,".

Signed and Sealed this

Twentieth Day of April, 2010

David J. Kappos
*Director of the United States Patent and Trademark Office*